US012023061B2

(12) United States Patent
Schneider et al.

(10) Patent No.: US 12,023,061 B2
(45) Date of Patent: Jul. 2, 2024

(54) MEDICAL INSTRUMENT

(71) Applicant: KARL STORZ SE & Co. KG, Tuttlingen (DE)

(72) Inventors: Janosz Schneider, Tuttlingen (DE); Dominik Längle, Tuttlingen (DE); Sven Axel Grüner, Tuttlingen (DE); Jochen Stefan, Tuttlingen (DE); Thorsten Ahrens, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/869,857

(22) Filed: Jul. 21, 2022

(65) Prior Publication Data

US 2023/0037240 A1 Feb. 2, 2023

(30) Foreign Application Priority Data

Jul. 28, 2021 (DE) ...................... 10 2021 119 563.2

(51) Int. Cl.
*A61B 17/29* (2006.01)
(52) U.S. Cl.
CPC .. *A61B 17/2909* (2013.01); *A61B 2017/2929* (2013.01); *A61B 2017/2947* (2013.01)
(58) Field of Classification Search
CPC .... A61B 2017/2926; A61B 2017/2929; A61B 17/0469; A61B 17/0483; A61B 2034/305; A61B 17/29
See application file for complete search history.

(56) References Cited

U.S. PATENT DOCUMENTS

| 5,643,293 | A | * | 7/1997 | Kogasaka | .......... | A61B 17/0469 |
| | | | | | | 606/139 |
| 6,312,435 | B1 | | 11/2001 | Wallace et al. | | |
| 9,561,028 | B1 | * | 2/2017 | Fan | ..................... | A61B 17/0482 |
| 10,512,454 | B2 | * | 12/2019 | Heneveld | .......... | A61B 17/0482 |

(Continued)

FOREIGN PATENT DOCUMENTS

| DE | 102019121092 A1 | 2/2021 |
| EP | 3824795 A1 | 5/2021 |

OTHER PUBLICATIONS

German Office Action for corresponding German Patent Application No. 10 2021 119 563.2, mailed May 11, 2022.

*Primary Examiner* — Mohamed G Gabr
*Assistant Examiner* — Aman Kumar Mann
(74) *Attorney, Agent, or Firm* — Jason H. Vick; Sheridan Ross, PC

(57) ABSTRACT

One embodiment relates to a medical instrument (1) with a hollow shaft (2), an actuating unit (4) arranged at the proximal end (3) of the shaft (2) and an instrument tip (6) with an instrument (7) arranged at the distal end (5) of the shaft (2), wherein the instrument (7) can be actuated via an actuating element (8) which is mounted in the shaft (2) in an axially displaceable manner, and wherein the actuating element (8) is operatively connected to the actuating unit (4) on the proximal side, and wherein the instrument tip (6) can be pivoted relative to the longitudinal axis (10) of the shaft (2) via a joint mechanism (9). According to one embodiment, the instrument tip (6) can be rotated endlessly, wherein a fixing device is provided on the instrument tip (6) with which the loose end (17, 23) of a sewing material (18, 24) can be fixed on the instrument tip (6).

10 Claims, 3 Drawing Sheets

(56) References Cited

U.S. PATENT DOCUMENTS

| | | | |
|---|---|---|---|
| 2005/0251165 A1* | 11/2005 | Vaughan | A61B 17/0401 606/153 |
| 2007/0239120 A1* | 10/2007 | Brock | A61B 34/20 604/272 |
| 2013/0098968 A1* | 4/2013 | Aranyi | A61B 17/068 227/177.1 |
| 2014/0039527 A1* | 2/2014 | Avelar | A61B 34/74 606/144 |
| 2016/0220238 A1* | 8/2016 | Heneveld | A61B 17/0482 |
| 2019/0029672 A1* | 1/2019 | Nobles | A61B 17/0491 |
| 2019/0125476 A1* | 5/2019 | Shelton, IV | A61B 17/1285 |
| 2019/0321028 A1* | 10/2019 | Dinino | A61B 17/0485 |
| 2020/0107835 A1* | 4/2020 | Sauer | A61B 17/1285 |
| 2020/0163733 A1* | 5/2020 | Smith | A61B 1/00087 |
| 2020/0375677 A1* | 12/2020 | Genova | A61B 34/30 |
| 2021/0038331 A1 | 2/2021 | Grüner | |

* cited by examiner

MEDICAL INSTRUMENT

CROSS-REFERENCE TO RELATED APPLICATIONS

This application claims the benefit under 35 U.S.C. 119(a) to German Patent Application No. 10 2021 119 563.2, filed 28 Jul. 2021, the disclosure of which is incorporated herein by reference in its entirety.

BACKGROUND

An exemplary embodiment relates to a medical instrument with a hollow shaft, an actuating unit arranged at the proximal end of the shaft and an instrument tip with an instrument arranged at the distal end of the shaft. The instrument can be actuated via an actuation element which is mounted in the shaft in an axially displaceable manner, wherein the actuation element is operatively connected to the actuation unit on the proximal side to enable the user to act on the actuation unit to mediate an actuation of the actuation element. By suitably actuating the actuating element, it is possible for the instrument tip to be pivoted relative to the longitudinal axis of the shaft via a joint mechanism.

A generic medical instrument is known from U.S. Pat. No. 6,312,435. However, with this instrument the rotational movement of the instrument tip is limited by the arrangement of the guide wires or guide ropes forming the actuating element. These guide wires or guide ropes are driven by a spindle. If the shaft is rotated by mechanical power transmission, the guide wires or guide ropes roll over or twist and form a cord. The effective length of the guide wires or guide ropes is shortened by the formation of cords, which leads to an increase in the tensile stress in the individual guide wires or guide ropes. If this tensile stress exceeds a permissible maximum tensile stress, the guide wires or guide ropes tear off. In this case, the medical instrument has no function. To prevent this, the maximum rotation of these instruments is limited to +/−315°.

This limitation of the maximum rotation is disadvantageous in particular when producing medical sutures using the instrument of the generic type. This is because the sewing material or the suture must be tightened after the sewing process is completed. The tightening of the suture is made even more difficult by the extremely narrow space in the surgical field, since, for example, it not possible to pull the end or loose end of the sewing material to the side with a gripper, forceps, a jaw part, or more precisely with two jaw part halves or two jaw branches due to the narrowness of the surgical field.

Therefore, one aspect of the disclosed technology is to create a medical instrument of the type mentioned above, with which the tightening of a sewing material is made easier, for example, to be able to tighten knots or the like.

The solution to this problem is characterised in that the instrument tip can be rotated endlessly, wherein a fixing device is provided in the instrument tip at the same time, with which the loose end of a sewing material can be fixed to the instrument tip. In principle, the design in which the drive of the instrument tip is designed to perform an endless rotation of the instrument tip is arbitrary. A type of design for the endless rotational drive of the instrument tip is described, for example, in DE 10 2019 121 092 A1.

The terms "end of the sewing material" and "loose end of the sewing material" are to be used synonymously and with the same meaning in the following and are accordingly interchangeable.

As soon as the loose end of a sewing material is fixed to the instrument tip, the instrument tip is driven in rotation and thereby the loose end of the sewing material is wound onto the instrument tip. This winding up of the sewing material means that it is increasingly shortened, so that the sewing material can be tightened, for example, to fix a knot or the like.

The manner in which the joint mechanism for pivoting the instrument tip is designed relative to the longitudinal axis of the shaft is fundamentally arbitrary. A particularly reliable and exact movement kinematics results when the joint mechanism consists of pivoting members arranged at the distal end of the shaft. The pivoting members are connected to a drive on the proximal side via guide wires or cables running in the longitudinal direction of the shaft such that a movement of the drive on the proximal side causes a corresponding relative movement of the pivoting members on the distal side and thus a pivoting of the instrument tip.

A spatially adjustable disc is preferably provided as the drive on the proximal side, with which the guide wires or guide ropes are moved.

To achieve an exact adjustment of the instrument tip when driving the adjustable disc and at the same time to enable high repeatability of the movement forms, according to a preferred embodiment, the drive for the spatially adjustable disc is designed as a motorisable drive.

To reliably fix the loose end of the sewing material to the instrument tip, a first preferred embodiment provides for the fixing device to be designed in the manner of an instrument provided with jaw parts. The jaw parts can be adjusted relative to each other between an open and a closed functional position. In the closed functional position of the jaw parts, the loose end of the sewing material is clamped between the jaw parts and fixed in this way. The jaw parts can then rotate about the common central axis in the closed functional position and thereby wind up the sewing material. Depending on the length of the loose end of the sewing material, the sewing material can then be tightened in this way, for example to fix a knot. The loose end of the sewing material can then be cut off with another instrument and removed from the surgical field with the medical instrument.

As an alternative to using an instrument with two jaw parts that can be adjusted relative to one another, the fixing device can also be designed in the manner of a clamping device with a clamping groove and a clamping slider. The clamping groove is to be designed in such a way that the loose end of the sewing material can be arranged in the clamping groove. The clamping slider in turn can be adjusted relative to the clamping groove between an open and a closed functional position. In the open functional position, the loose end of the sewing material is inserted into the clamping groove. The loose end of the sewing material can then be fixed by moving the clamping slider into the closed functional position between an inner surface of the clamping groove and a corresponding clamping surface on the clamping slider. Once the suture is secured, the instrument tip can be driven in rotation to wind the suture onto the instrument tip and thereby tighten it.

To achieve clean guidance of the sewing material when it is wound onto the instrument tip, it is particularly advantageous if a waist is provided on the outside of the instrument tip. As a result of this waist, the sewing material is guided in the direction of the smallest diameter of the scaled area when it is wound onto the instrument tip, and clean winding of the sewing material is achieved.

BRIEF DESCRIPTION OF THE DRAWINGS

Further features and advantages of the invention result from the associated drawings, in which two exemplary embodiments of a medical instrument according to the invention are illustrated only as examples, without restricting the invention to these exemplary embodiments. The drawings show the following.

DETAILED DESCRIPTION

Figure 1:
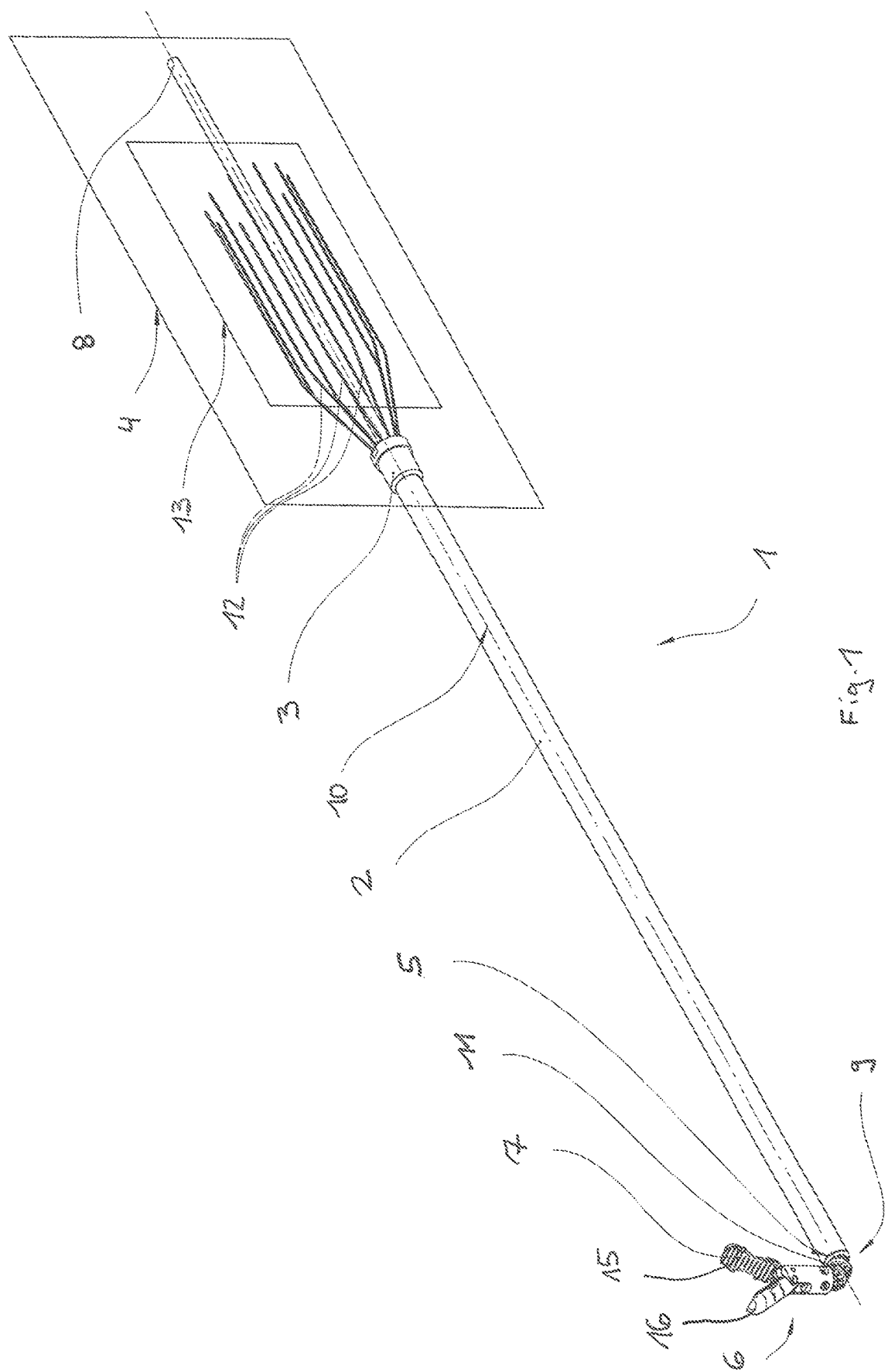
FIG. 1 a schematic perspective side view of a medical instrument according to an exemplary embodiment.

FIG. 1 schematically shows a medical instrument 1 with a hollow shaft 2, an actuating unit 4 arranged at the proximal end 3 of the shaft 2, only illustrated schematically, and an instrument tip 6 arranged at the distal end 5 of the shaft 2 with an instrument 7, wherein the instrument 7 can be actuated via an actuating element 8 which is mounted in the shaft 2 in an axially displaceable manner. The actuating element 8 is operatively connected to an actuating unit 4 on the proximal side.

The actuation unit 4 can be a manually actuable handling unit or a unit designed for robotic use, that is, one that can also be actuated without manual intervention. The actuation unit used in each case enables an endless rotary drive, as illustrated in FIG. 1, of the angled instrument tip 6. For this purpose, for example, an actuation unit can be used, as described in DE 10 2019 121 092 A1. The instrument 7 of the instrument tip 6 can be a tool provided with jaw parts 15. The instrument tip 6 can be pivoted relative to the longitudinal axis 10 of the shaft 2 via a joint mechanism 9, wherein the joint mechanism 9 consists of pivoting members 11 arranged at the distal end of the shaft 5, which are connected via guide wires 12 or guide ropes running in the longitudinal direction of the shaft 2 with a drive 13 arranged at the proximal end 3 of the shaft 2, which causes a movement of the drive 13 on the proximal side and corresponding relative movements of the pivoting members 11 on the distal side and thus a pivoting of the instrument tip 6. A suitable drive 13 is described, for example, in DE 10 2019 121 092 A1, to which express reference is made here.

Figure 2:
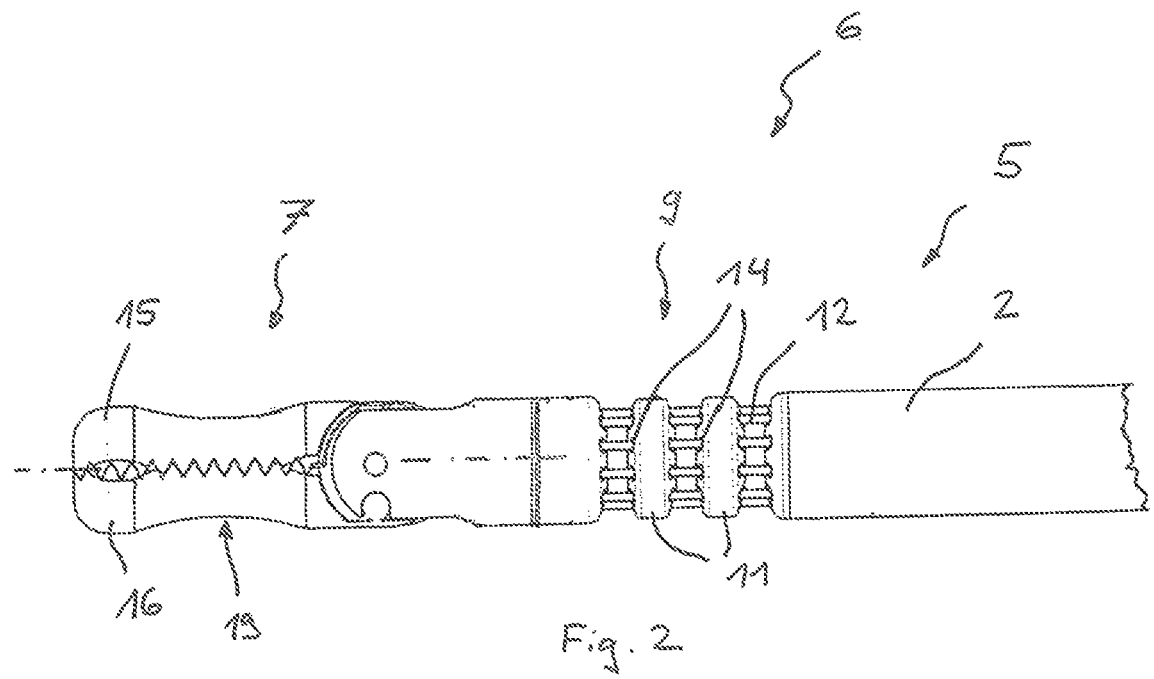
FIG. 2 shows the instrument tip 6 in an enlarged side view. The shaft 2 can be seen at the distal end 5, at which the guide wires 12 or guide ropes emerge from the shaft 2 and are passed through recesses 14 in two pivoting members 11, which form the joint mechanism 9. The ends of the guide wires 12 or guide ropes are fixed to the instrument tip 6. The instrument 7 at the instrument tip 6 is formed by two jaw parts 15 and 16. At least one of the two jaw parts 15 and 16 is pivotably mounted on the instrument tip 6 and can be pivoted between a closed position shown in FIG. 2 and an open position, not shown, by axial adjustment of the actuating element 8.

FIG. 2 shows the instrument tip 6 in an enlarged side view. The shaft 2 can be seen at the distal end 5, at which the guide wires 12 or guide ropes emerge from the shaft 2 and are passed through recesses 14 in two pivoting members 13, which form the joint mechanism 9. The ends of the guide wires 12 or guide ropes are fixed to the instrument tip 6. The instrument 7 at the instrument tip 6 is formed by two jaw parts 15 and 16. At least one of the two jaw parts 15 and 16 is pivotably mounted on the instrument tip 6 and can be pivoted between a closed position shown in FIG. 2 and an open position, not shown, by axial adjustment of the actuating element 8.

Figure 3:
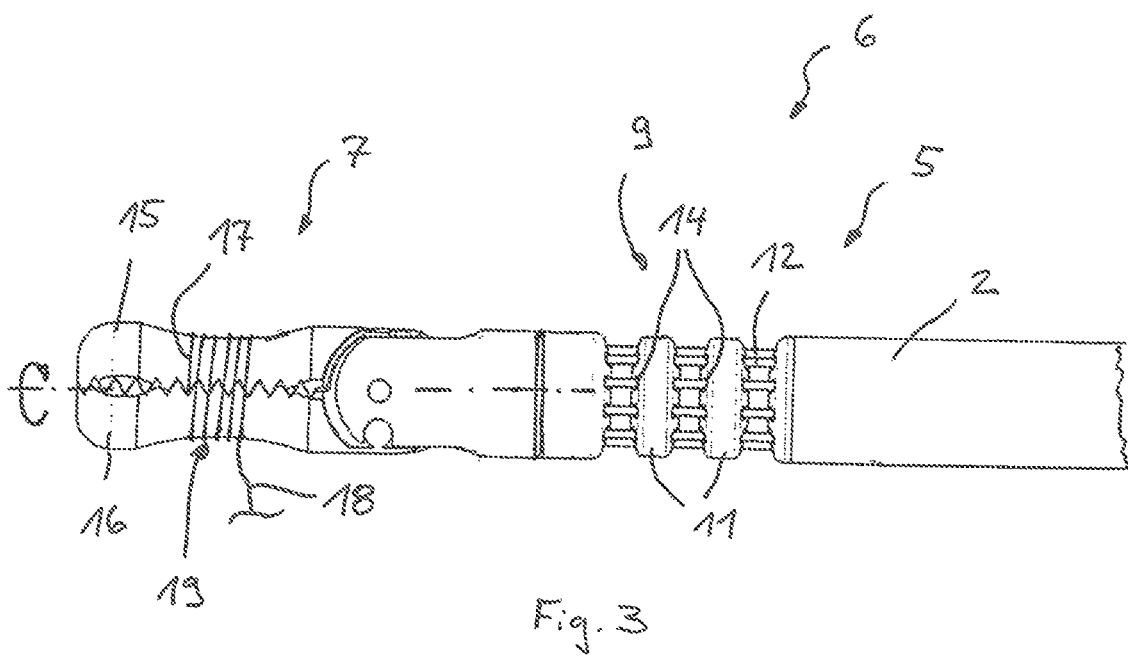
FIG. 3 the instrument tip according to FIG. 2 after winding the loose end of a suture.

FIG. 3 shows the instrument tip 6 in its function as a fixing device for fixing the loose end 17 of a sewing material 18. First, the loose end 17 is brought between the jaw parts 15 and 16 by opening the components 15 and 16 and then, by actuating the actuating element 8, the fixing device formed by the jaw parts 15 and 16 is moved into its closed functional position shown in FIG. 3. The loose end 17 is then fixed between the jaw parts 15 and 16 in this closed functional position. The sewing material 18 can then be wound onto a waist 19 on the outer circumference of the instrument tip 7 by rotating the instrument 6, for example driven by the rotation of the shaft 2. By winding up the loose end 17, the sewing material 18 can be tightened in a minimal space in the surgical field, for example to tighten a knot.

Figure 4:
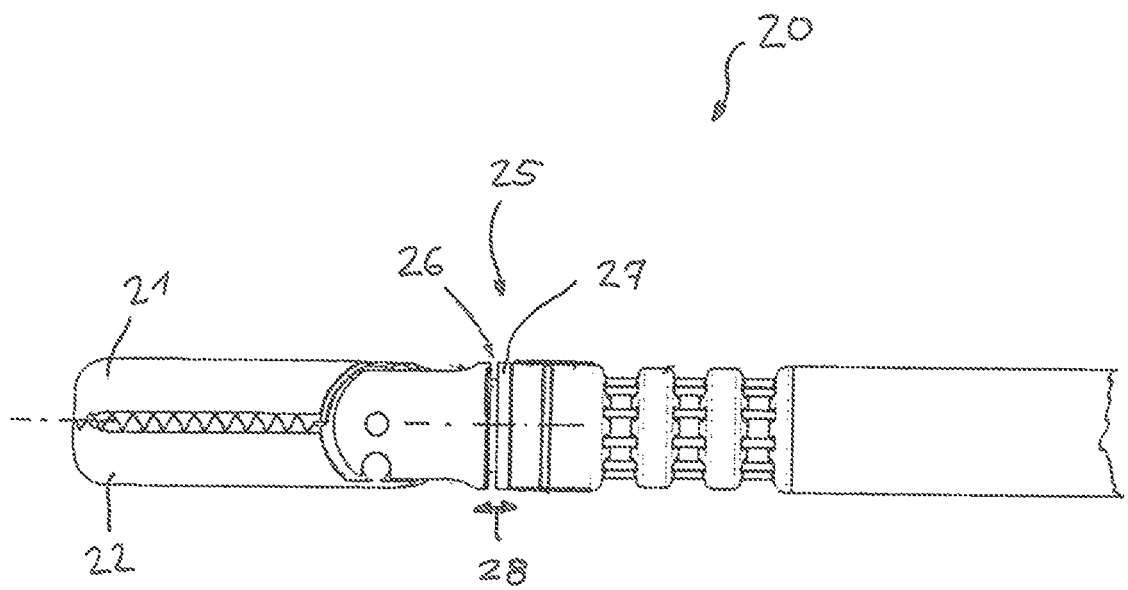
FIG. 4 a second embodiment of an instrument tip for use on an instrument according to an exemplary embodiment.

FIG. 4 shows a second embodiment 20 of an instrument tip for tightening sewing material 24, which is achieved by a rotary drive of the instrument tip 20. Two jaw parts 21 and 22 are in turn provided on the instrument tip 20 and can be opened and closed by means of the actuating element 8. To fix the loose end 23 (see FIG. 5) of a sewing material 24, a fixing device is used on the instrument tip 20, which is designed in the manner of a clamping device 25. The clamping device 25 consists essentially of a clamping groove 26, in which a clamping slider 27 between the open functional position shown in FIG. 4 and the closed functional position shown in FIG. 5 can be adjusted along the movement arrow 28. For the adjustment of the clamping slider 27, an additional actuating device is provided on the instrument 1, which is not illustrated in detail in the drawings.

Figure 5:
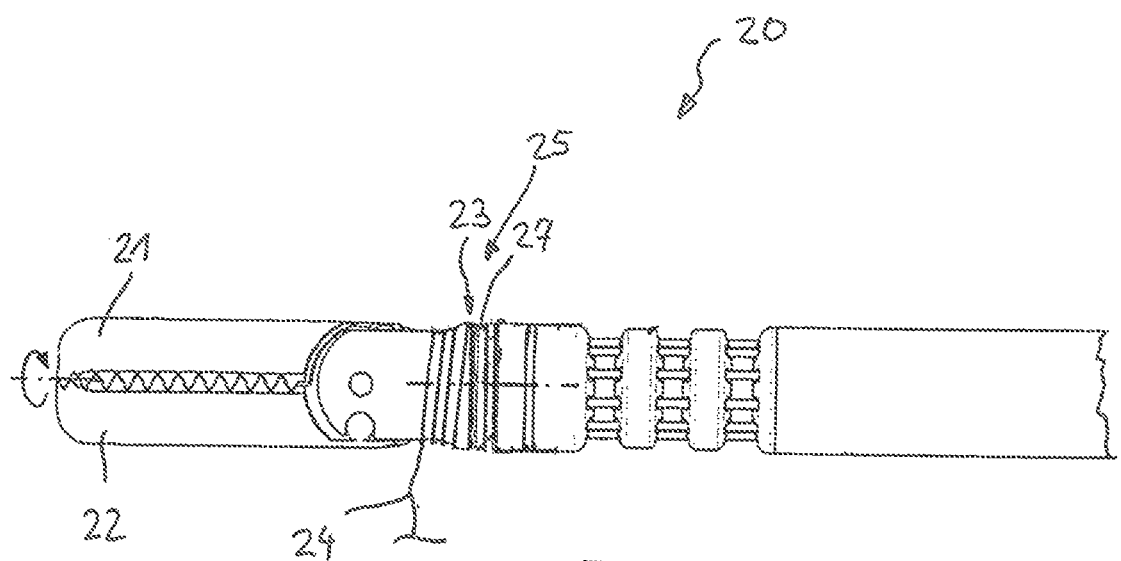
FIG. 5 the instrument tip according to FIG. 4 after winding the loose end of a suture.

As illustrated in FIG. 5, to fix the loose end 23 of the sewing material 24, the clamping slider 27 is first opened and the loose end 23 is inserted into the opened clamping groove 26. Then the clamping slider 27 is inserted into the closed functional position shown in FIG. 5, the loose end 23 adjusted and thereby fixed between the lateral inner surface of the clamping groove 26 and the clamping slider 27. The sewing material 24 can then be wound onto the outer circumference of the instrument tip 20 by rotating the instrument tip 20 and the sewing material 24 can thereby be tightened to tighten a knot, for example.

LIST OF REFERENCE NUMBERS

1 Medical instrument
2 Shaft
3 Proximal end (shaft)
4 Operating unit
5 Distal end (shaft)
6 Instrument tip
7 Instrument
8 Actuating element
9 Joint mechanism
10 Longitudinal axis
11 Pivoting member
12 Guide wire
13 Drive
14 Recess
15 Jaw part 16 Jaw part
17 Loose end
18 Sewing material
19 Waist
20 Instrument tip
21 Jaw part
22 Jaw part
23 Loose end
24 Sewing material
25 Clamping device
26 Clamping groove
27 Clamping slider
28 Movement arrow

The invention claimed is:

1. A medical instrument comprising:
a hollow shaft having a distal end and a proximate end,
an actuating unit arranged at the proximal end of the shaft and configured for an endless rotary drive,
an instrument tip with an instrument arranged at the distal end of the shaft, and
an actuating element mounted in the shaft in an axially displaceable manner, the actuating element operatively connected to the actuating unit on the proximal end, wherein the instrument tip is pivotable relative to a longitudinal axis of the shaft via a joint mechanism, the joint mechanism comprising a plurality of pivoting members with a plurality of guide wires running therethrough,
wherein the instrument tip is configured to be endlessly rotated, and a fixing device is provided on the instrument tip and is configured to hold a loose end of a sewing material in a clamping groove, the instrument tip including the clamping groove around a circumference of the instrument tip, and a cylindrical clamping slider configured to be slid longitudinally relative to the instrument tip between an open and a closed functional position, the clamping slider configured to secure a loose end of sewing material between an inner surface of the clamping groove and the clamping slider, the cylindrical clamping slider configured to be slid longitudinally on an exterior portion of the instrument tip.

2. The medical instrument according to claim 1, wherein the joint mechanism includes the plurality of pivoting members arranged at the distal end of the shaft, the plurality of pivoting members connected to a drive on the proximal side via a plurality of guide wires running in the longitudinal direction of the shaft, wherein, in operation, a movement of the drive on the proximal side causes a corresponding relative movement of the plurality of pivoting members on the distal side and thus a pivoting of the instrument tip.

3. The medical instrument according to claim 2, one or more of the first and second jaw parts include teeth.

4. The medical instrument according to claim 3, wherein the teeth extend over an entirety of an inner surface of the first and second jaw parts.

5. The medical instrument according to claim 1, wherein the fixing device comprises jaw parts, wherein the jaw parts are adjustable relative to one another between an open and a closed functional position, and wherein the loose end of the sewing material can be fixed between the jaw parts in the closed functional position.

6. A medical instrument comprising:
an elongated hollow shaft having a distal end and a proximate end, the elongated shaft accommodating a plurality of guide wires,
an actuating unit arranged at the proximal end of the shaft and configured for an endless rotary drive,
an instrument tip with an instrument arranged at the distal end of the shaft, and
an actuating element mounted in the shaft in an axially displaceable manner, the actuating element operatively connected to the actuating unit on the proximal end, wherein the instrument tip is pivotable relative to a longitudinal axis of the shaft via a joint mechanism, the joint mechanism comprising a plurality of pivoting members with the plurality of guide wires running therethrough,
wherein the instrument tip can be endlessly rotated to facilitate securing of a sewing material, and a fixing device is provided on the instrument tip, and is configured to hold a loose end of a sewing material in a clamping groove, the instrument tip including a clamping groove around a circumference of the instrument tip, and a cylindrical clamping slider configured to be slid longitudinally relative to the instrument tip between an open and a closed functional position, the clamping slider configured to secure a loose end of sewing material between an inner surface of the clamping groove and the clamping slider, the cylindrical clamping slider configured to be slid longitudinally on an exterior portion of the instrument tip.

7. The medical instrument according to claim 6, wherein the joint mechanism includes the plurality of pivoting members arranged at the distal end of the shaft, the plurality of pivoting members connected to a drive on the proximal side via a plurality of guide wires running in the longitudinal direction of the shaft, wherein, in operation, a movement of the drive on the proximal side causes a corresponding relative movement of the plurality of pivoting members on the distal side and thus a pivoting of the instrument tip.

8. The medical instrument according to claim 7, wherein one or more of the first and second jaw parts include teeth.

9. The medical instrument according to claim 8, wherein the teeth extend over an entirety of an inner surface of the first and second jaw parts.

10. The medical instrument according to claim 6, wherein the fixing device comprises jaw parts, wherein the jaw parts are adjustable relative to one another between an open and a closed functional position, and wherein the loose end of the sewing material can be fixed between the jaw parts in the closed functional position.

* * * * *